(12) United States Patent
Lee et al.

(10) Patent No.: US 11,559,239 B2
(45) Date of Patent: Jan. 24, 2023

(54) ELECTRONIC DEVICE INCLUDING ELECTRICALLY CONDUCTIVE CONNECTION MEMBER

(71) Applicant: Samsung Electronics Co., Ltd., Suwon-si (KR)

(72) Inventors: June Lee, Suwon-si (KR); Junhui Lee, Suwon-si (KR); Yongyi Kim, Suwon-si (KR); Seunghyun Cho, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 287 days.

(21) Appl. No.: 16/860,354

(22) Filed: Apr. 28, 2020

(65) Prior Publication Data
US 2021/0000364 A1 Jan. 7, 2021

(30) Foreign Application Priority Data

Jul. 2, 2019 (KR) .................. 10-2019-0079161

(51) Int. Cl.
*H05K 1/18* (2006.01)
*H01H 13/52* (2006.01)
(Continued)

(52) U.S. Cl.
CPC ............ *A61B 5/332* (2021.01); *H01H 13/04* (2013.01); *H01H 13/14* (2013.01); *H01H 13/52* (2013.01);
(Continued)

(58) Field of Classification Search
CPC ......... A61B 5/332; A61B 5/339; A61B 5/282; A61B 5/681; A61B 2562/166;
(Continued)

(56) References Cited

U.S. PATENT DOCUMENTS 4,033,110 A * 7/1977 Sagarino ................ G04G 17/02
968/878
4,142,287 A * 3/1979 Grabbe .................. H05K 3/326
968/878
(Continued)

FOREIGN PATENT DOCUMENTS

EP          3 451 117 A1    3/2019
KR    10-2016-0044270 A    4/2016

OTHER PUBLICATIONS

International Search Report dated Aug. 3, 2020, issued in International Application No. PCT/KR2020/005585.
(Continued)

*Primary Examiner* — Anatoly Vortman
(74) *Attorney, Agent, or Firm* — Jefferson IP Law, LLP

(57) ABSTRACT

An electronic device is provided. The electronic device includes a housing, a printed circuit board disposed inside the housing and including a first face and a second face that faces away from the first face, a connection member disposed on the first face and electrically connected to the printed circuit board, a switch member disposed on the first face and at least partially overlaps the connection member when viewed from above the first face, and a button member including an electrically conductive member, and disposed to be capable of operating the switch member. The electrically conductive member is electrically connected to the connection member.

20 Claims, 10 Drawing Sheets

(51) Int. Cl.
*H01H 13/14* (2006.01)
*H01H 13/04* (2006.01)
*A61B 5/332* (2021.01)
*A61B 5/00* (2006.01)
*A61B 5/282* (2021.01)
*A61B 5/339* (2021.01)

(52) U.S. Cl.
CPC .............. *H05K 1/181* (2013.01); *A61B 5/282* (2021.01); *A61B 5/339* (2021.01); *A61B 5/681* (2013.01); *A61B 2562/166* (2013.01); *A61B 2562/227* (2013.01); *H01H 2207/03* (2013.01); *H05K 2201/10053* (2013.01)

(58) Field of Classification Search
CPC .. A61B 2562/227; H01H 13/04; H01H 13/14; H01H 13/52; H01H 2207/03; H05K 1/181; H05K 2201/10053; G04G 21/025
USPC ........................................................ 600/509
See application file for complete search history.

(56) References Cited

U.S. PATENT DOCUMENTS

| | | | | |
|---|---|---|---|---|
| 4,238,848 A * | 12/1980 | Yamaguchi | ............ | G04G 17/02 968/878 |
| 4,272,838 A * | 6/1981 | Kasama | ............ | H01M 50/216 968/878 |
| 5,438,315 A * | 8/1995 | Nix | .................... | G08B 21/0297 340/539.11 |
| 6,527,610 B1 * | 3/2003 | Hornsby | .............. | G04G 9/0064 446/175 |
| 7,646,677 B2 * | 1/2010 | Nakamura | ............ | G04G 21/00 368/185 |
| 8,506,327 B2 * | 8/2013 | Jol | ........................ | H01R 13/405 361/737 |
| 8,576,561 B2 * | 11/2013 | Myers | .................. | H05K 5/0208 343/702 |
| 8,964,511 B2 * | 2/2015 | Fujisawa | ................ | G04C 10/02 368/47 |
| 9,947,491 B1 * | 4/2018 | Thome | ..................... | H01H 3/60 |
| 10,114,342 B2 * | 10/2018 | Kim | .................... | G04C 17/0091 |
| 10,610,157 B2 * | 4/2020 | Pandya | ............. | A61B 5/02427 |
| 2015/0041289 A1 | 2/2015 | Ely | | |
| 2015/0195009 A1 | 7/2015 | Wang et al. | | |
| 2016/0106333 A1 | 4/2016 | Kang et al. | | |
| 2016/0234362 A1 * | 8/2016 | Moon | .................. | H04M 1/0202 |
| 2017/0178834 A1 | 6/2017 | Lagorgette et al. | | |
| 2017/0215743 A1 | 8/2017 | Meer et al. | | |
| 2017/0315584 A1 * | 11/2017 | Lee | ...................... | H01Q 1/273 |
| 2018/0220972 A1 * | 8/2018 | Jeong | ................... | A61B 5/7445 |
| 2018/0329368 A1 | 11/2018 | Ely et al. | | |
| 2019/0072912 A1 | 3/2019 | Pandya et al. | | |
| 2019/0074724 A1 | 3/2019 | Wittenberg et al. | | |
| 2020/0064779 A1 | 2/2020 | Pandya et al. | | |
| 2021/0037126 A1 * | 2/2021 | Yoo | ..................... | H04M 1/0266 |

OTHER PUBLICATIONS

European Search Report dated Jul. 6, 2022, issued in European Patent Application No. 20835302.9.

* cited by examiner

ELECTRONIC DEVICE INCLUDING ELECTRICALLY CONDUCTIVE CONNECTION MEMBER

CROSS-REFERENCE TO RELATED APPLICATION(S)

This application is based on and claims priority under 35 U.S.C. § 119(a) of a Korean patent application number 10-2019-0079161, filed on Jul. 2, 2019, in the Korean Intellectual Property Office, the disclosure of which is incorporated by reference herein in its entirety.

BACKGROUND

1. Field

The disclosure relates to an electronic device. More particularly, the disclosure relates to an electronic device capable of measuring or detecting a user's biometric information.

2. Description of Related Art

Typically, an electronic device may mean a device that performs a specific function according to a program provided therein (e.g., an electronic scheduler, a portable multimedia reproducer, a mobile communication terminal, a tablet personal computer (PC), an image/sound device, a desktop/laptop PC, or a vehicle navigation system), as well as a home appliance. As the integration degree of electronic devices has increased and super-high speed and large capacity wireless communication has become popular, various functions have recently been provided in a single electronic device, such as a mobile communication terminal. For example, various functions, such as an entertainment function (e.g., a game function), a multimedia function (e.g., a music/video reproducing function), a communication and security function for mobile banking, a schedule management function, or an e-wallet function, are integrated in a single electronic device, in addition to a communication function. With the development of electronic and communication technology, electronic devices have been reduced in size and weight, so that the electronic devices can be used without any inconvenience even in the state in which the electronic devices are worn on a body.

The above information is presented as background information only to assist with an understanding of the disclosure. No determination has been made, and no assertion is made, as to whether any of the above might be applicable as prior art with regard to the disclosure.

SUMMARY

Since an electronic device wearable on a human body may be maintained for a considerable amount of time in the state of being in contact with the user's body, the electronic device may be useful for medical or health care. For example, depending to sensors mounted therein, the electronic device may detect the user's biological information, such as a photo plethysmograph (PPG), a sleep interval, a skin temperature, a heart rate, or an electrocardiogram. The detected biometric information may be stored in the electronic device or transmitted to a medical institution in real time to be used for health care of the user.

However, in an electronic device that is small enough to be used without discomfort even when worn on a body, there may be a limitation in arranging sensors or electrodes for detecting biometric information. For example, in electrocardiogram measurement, when a plurality of electrodes is disposed at sufficient intervals, accuracy of the detected biometric information may be ensured. However, there may be a limitation in securing intervals between electrodes in a miniaturized electronic device. Here, the term "intervals between electrodes" may mean intervals between body portions with which the electrodes come into contact. In some embodiments of the disclosure, when the signal path formed between the electrodes on the user's body is formed closer to the heart, biometric information, such as an electrocardiogram may be more accurate. However, it may be difficult to form such a signal path only with a miniaturized electronic device.

Aspects of the disclosure are to address at least the above-mentioned problems and/or disadvantages and to provide at least the advantages described below. Accordingly, an aspect of the disclosure is to provide an electronic device capable of detecting biometric information, such as a photo plethysmograph, a sleep interval, a skin temperature, a heart rate, or an electrocardiogram.

Another aspect of the disclosure is to provide an electronic device capable of improving accuracy of biometric information.

Additional aspects will be set forth in part in the description which follows and, in part, will be apparent from the description, or may be learned by practice of the presented embodiments.

In accordance with an aspect of the disclosure, an electronic device is provided. The electronic device includes a housing, a printed circuit board disposed inside the housing and including a first face and a second face that faces away from the first face, a connection member disposed on the first face and electrically connected to the printed circuit board, a switch member disposed on the first face and at least partially overlaps the connection member when viewed from above the first face, and a button member including an electrically conductive member, and disposed to be capable of operating the switch member. The electrically conductive member is electrically connected to the connection member.

In accordance with another aspect of the disclosure, an electronic device is provided. The electronic device includes a housing, a binding member connected to at least a portion of the housing and configured to detachably attach the housing to a user's body, a printed circuit board disposed inside the housing, a connection member disposed on the printed circuit board and electrically connected to the printed circuit board, a button member including an electrically conductive member electrically connected to the connection member, at least one processor disposed inside the housing, and a biometric sensor at least partially exposed to an outside of the housing. The at least one processor is configured to detect a user's biometric information via the electrically conductive member and the biometric sensor.

According to various embodiments disclosed herein, the electronic device includes one or more electrodes, which come into contact with the user's body even in the state in which the electronic device is merely worn, and an electronic device capable of coming into contact with a body portion other than the portion in which the electronic device is worn. Thus, in detecting biometric information, such as an electrocardiogram, it is possible to improve the accuracy of the biometric information. In an embodiment of the disclosure, a portion of a key or button disposed on the electronic device is made of an electrically conductive material, and can be used as an electrode for measuring biometric information. For example, an electrode for detecting biometric information is disposed without lowering the degree of freedom in designing the electronic device. Thus, it is possible to improve the accuracy of detected biometric information. A connection member is disposed on a printed circuit board, which is disposed to correspond to a key or button as an input device and electrically connects the electrode on the key or button to the printed circuit board. Thus, it is easy to secure wires for connecting an electrode for detecting biometric information to a circuit unit (e.g., a processor).

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, like reference numerals will be understood to refer to like parts, components, and structures.

DETAILED DESCRIPTION

Figure 1:
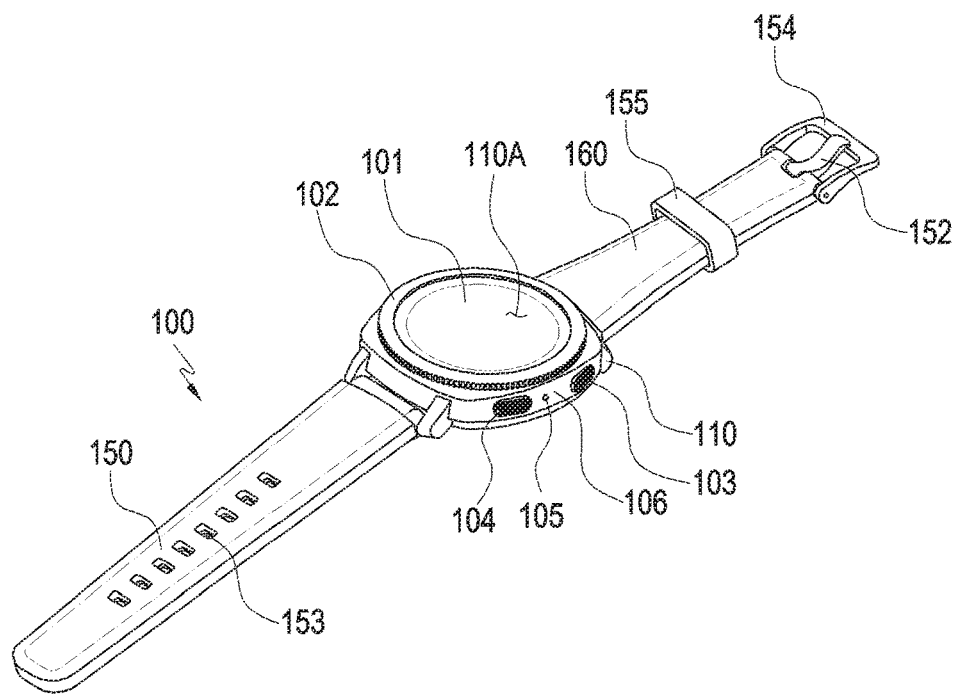
FIG. 1 is a front side perspective view illustrating an electronic device according to an embodiment of the disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program) including one or more instructions that are stored in a storage medium (e.g., internal memory or external memory) that is readable by a machine (e.g., the electronic device). For example, a processor (e.g., the processor) of the machine (e.g., the electronic device) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

FIG. 1 is a front side perspective view illustrating an electronic device according to an embodiment of the disclosure.

Figure 2:
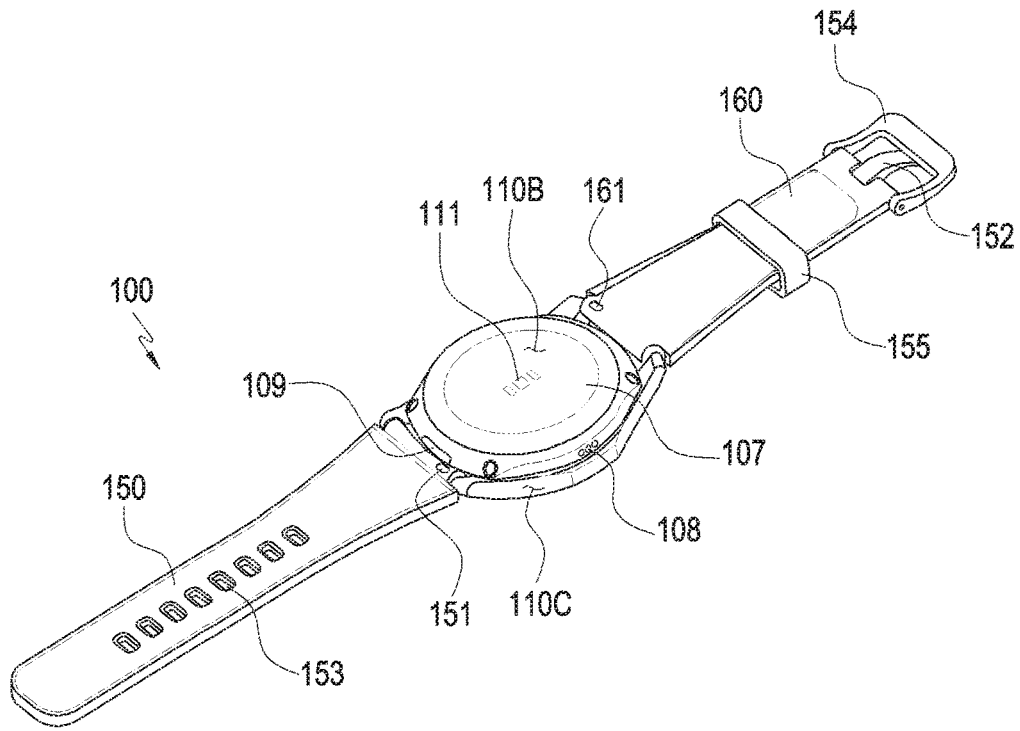
FIG. 2 is a rear side perspective view illustrating an electronic device according to an embodiment of the disclosure.

FIG. 2 is a rear side perspective view illustrating an electronic device according to an embodiment of the disclosure.

Referring to FIGS. 1 and 2, an electronic device 100 according to an embodiment of the disclosure may include a housing 110 including a front face 110A, a rear face 110B, and a side face 110C surrounding a space between the front face 110A and the rear face 110B, and binding members 150 and 160 connected to at least a portion of the housing 110 and configured to detachably bind the electronic device 100 on a portion of a user's body (e.g., a wrist or an ankle). In another embodiment (not illustrated) of the disclosure, the term "housing" may refer to a structure forming a part of the front face 110A, the rear face 110B, and the side face 110C.

According to various embodiments of the disclosure, at least a portion of the front face 110A may be formed by a substantially transparent front plate 101 (e.g., a glass plate or a polymer plate including various coating layers). The rear face 110B may be formed of a substantially opaque rear plate 107. The rear plate 107 may be formed of, for example, coated or colored glass, ceramic, a polymer, a metal (e.g., aluminum, stainless steel (STS), or magnesium), or a combination of two or more of these materials. The side face 110C may be formed by a side bezel structure 106 (or a "side member") coupled to the front plate 101 and the rear plate 107 and including a metal and/or a polymer. In some embodiments of the disclosure, the rear plate 107 and the side bezel structure 106 may be integrally formed, and may include the same material (e.g., a metallic material, such as aluminum). The binding members 150 and 160 may be formed of various materials and in various shapes. The binding members 150 and 160 may be formed by coupling a plurality of integrated-type unit links to be movable with respect to each other using a woven material, leather, rubber, urethane, metal, ceramic, or a combination of at least two of the above-mentioned materials.

According to an embodiment of the disclosure, the electronic device 100 may include at least one of a display (e.g., a display device 202 in FIG. 2), audio modules 105 and 108, a sensor module 111, key input devices 102, 103, and 104, and a connector hole 109. In some embodiments of the disclosure, in the electronic device 100, at least one of the components (e.g., the key input devices 102, 103, and 104, the connector hole 109, or the sensor module 111) may be omitted, or other components may be additionally included.

The display may be exposed through, for example, a substantial portion of the front plate 101. The shape of the display may correspond to the shape of the front plate 101, and may be any of various shapes, such as a circle, an ellipse, and a polygon. The display may be coupled to or disposed adjacent to a touch sensing circuit, a pressure sensor capable of measuring the intensity (pressure) of a touch, and/or a fingerprint sensor.

According to various embodiments of the disclosure, the audio modules 105 and 108 may include a microphone hole 105 and a speaker hole 108. The microphone hole 105 may include a microphone disposed therein so as to acquire external sound, and in some embodiments of the disclosure, multiple microphones may be disposed therein so as to detect the direction of sound. The speaker hole 108 may be used for an external speaker and a phone call receiver. In some embodiments of the disclosure, the speaker hole 108 and the microphone hole 105 may be implemented as a single hole, or a speaker may be included without a speaker hole 108 (e.g., a piezo speaker).

According to various embodiments of the disclosure, the sensor module 111 may generate an electrical signal or a data value corresponding to an internal operating state of the electronic device 100 or an external environmental state. The sensor module 111 may include, for example, a biometric sensor module 111 (e.g., a heart rate monitor (HRM) sensor) disposed on the rear face 110B of the housing 110. The electronic device 100 may further include at least one of sensors (not illustrated in the drawings), such as a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illuminance sensor. In an embodiment of the disclosure, the sensor module 111 may include a plurality of electrodes, and when the user wears the electronic device 100 using the binding members 150 and 160, at least one of the electrodes of the sensor module 111 may be brought into contact with the user's body.

According to various embodiments of the disclosure, the key input devices 102, 103, and 104 may include a wheel key 102 disposed on the front face 110A of the housing 110 and configured to be rotatable in at least one direction, and/or side key buttons 103 and 104 disposed on the side face 110C of the housing 110. The wheel key 102 may have a shape (e.g., a circular frame) corresponding to the shape of the front plate 101. In another embodiment of the disclosure, the electronic device 100 may not include some or all of the above-mentioned key input devices 102, 103, and 104, and a non-included key input device 102, 103, or 104 may be implemented in another form, such as a soft key on the display.

According to various embodiments of the disclosure, the connector hole 109 may accommodate a connector (e.g., a universal serial bus (USB) connector) configured to transmit and receive power and/or data to and from an external electronic device, and may include another connector hole (not illustrated) capable of accommodating a connector configured to transmit and receive an audio signal to and from an external electronic device. The electronic device 100 may further include, for example, a connector cover (not illustrated) that covers at least a portion of the connector hole 109 and blocks entry of external foreign matter into the connector hole.

According to various embodiments of the disclosure, the binding members 150 and 160 may be detachably bound to at least a portion of the housing 110 using locking members 151 and 161, respectively. In an embodiment of the disclosure, each of the binding members 150 and 160 may include at least one of a fixing member 152, fixing member fastening holes 153, a band guide member 154, and a band fixing ring 155.

According to various embodiments of the disclosure, the fixing member 152 may be configured to fasten the housing 110 and the binding members 150 and 160 to the user's body part (e.g., a wrist or an ankle). The fixing member fastening holes 153 allow the housing 110 and the binding members 150 and 160 to be fixed to a portion of the user's body in cooperation with the fixing member 152. The band guide member 154 is configured to limit the movement range of the fixing member 152 when the fixing member 152 is fastened to any of the fixing member fastening holes 153 so as to ensure that the binding members 150 and 160 are brought into close contact with and bound on the user's body part. The band fixing ring 155 is capable of limiting the movement range of the binding members 150 and 160 in the state in which the fixing member 152 and the fixing member fastening hole 153 are fastened to each other.

Figure 3:
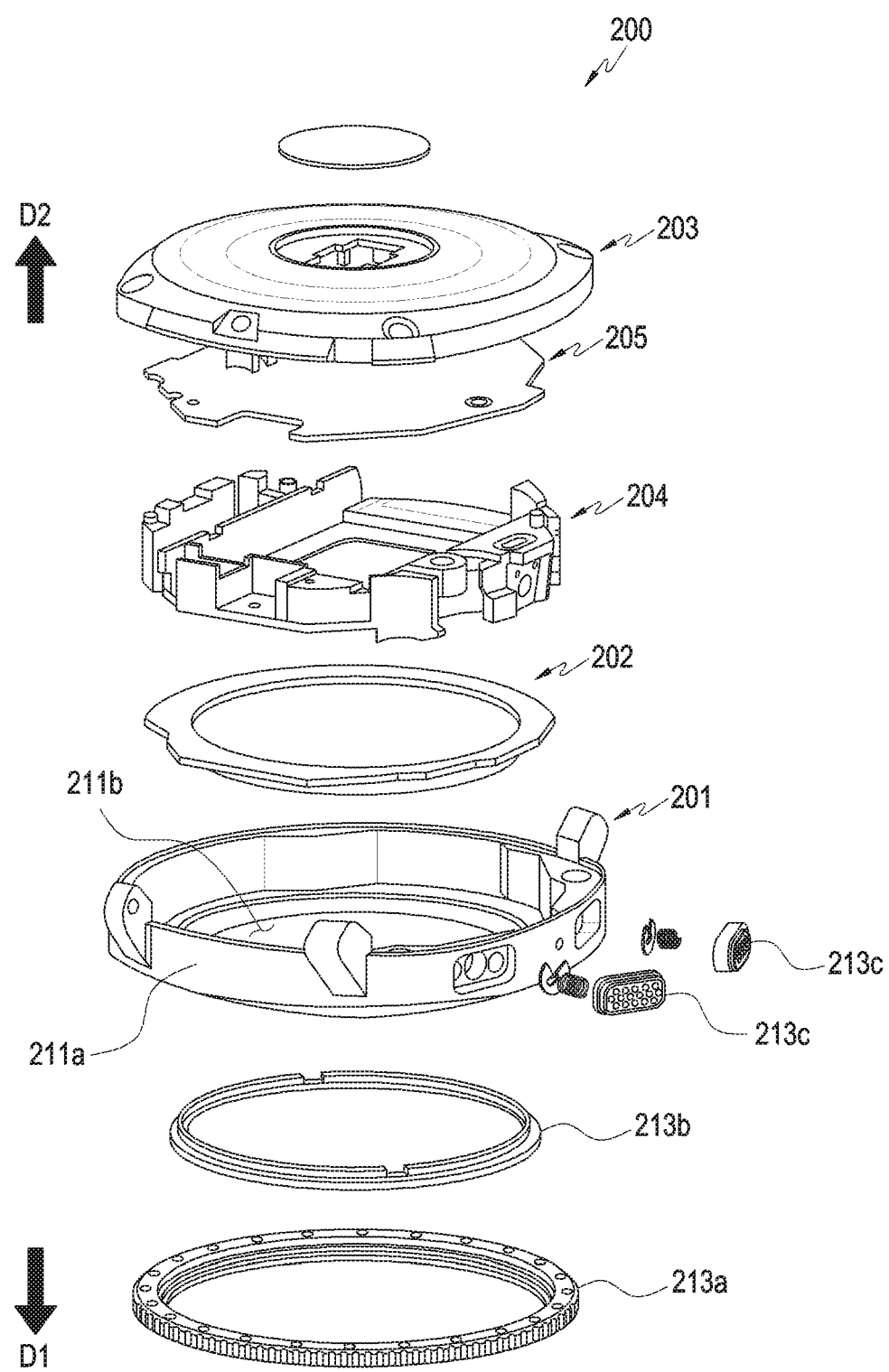
FIG. 3 is an exploded perspective view illustrating an electronic device according to an embodiment of the disclosure.

FIG. 3 is an exploded perspective illustrating an electronic device according to an embodiment of the disclosure.

Figure 4:
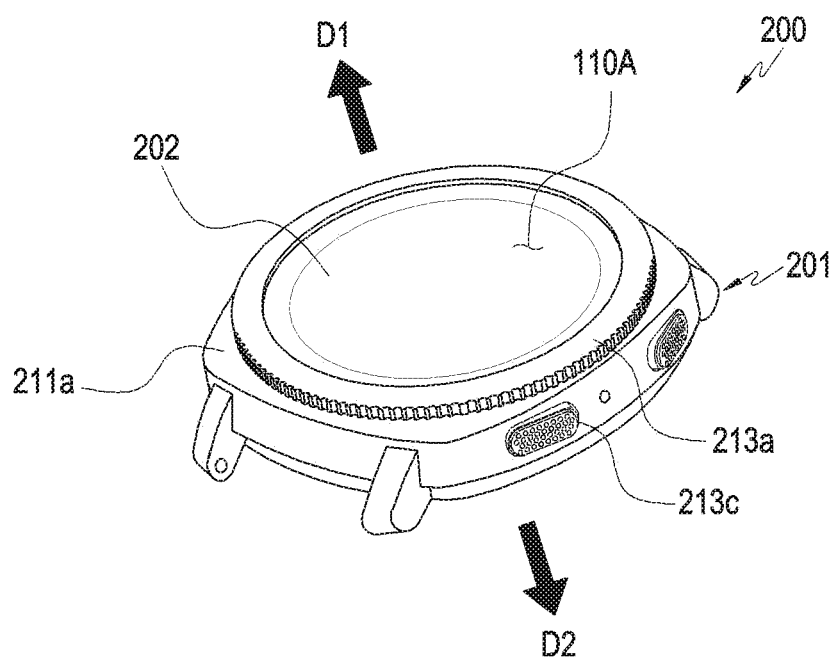
FIG. 4 is a perspective view illustrating an electronic device in an assembled state according to an embodiment of the disclosure.

FIG. 4 is a perspective view illustrating an electronic device in an assembled state according to an embodiment of the disclosure.

Referring to FIGS. 3 and 4, an electronic device 200 (e.g., the electronic device 100 in FIG. 1 or FIG. 2) according to an embodiment of the disclosure may include a housing 201 (e.g., the housing 110 in FIG. 1 or FIG. 2), a support member 204 and/or a first printed circuit board 205. In some embodiments of the disclosure, the housing 201 may at least partially include an electrically conductive material, and may transmit or receive a wireless signal when the electrically conductive material of the housing 201 is electrically connected to the first printed circuit board 205. For example, a portion of the housing 201 may function as an antenna of the electronic device 200.

According to an embodiment of the disclosure, at least one of the components of the electronic device 200 may be the same or similar to at least one of the components of the electronic device 100 of FIG. 1 or FIG. 2, and a redundant description may be omitted in the following description. According to another embodiment of the disclosure, the electronic device 200 may include the binding members 150 and 160 of FIG. 1 or FIG. 2, whereby the user is capable of carrying or using the electronic device 200 in the state in which the electronic device 200 is worn on the user's body.

According to various embodiments of the disclosure, the housing 201 may include a front face (e.g., the front face 110A in FIG. 1) oriented in a first direction D1, a rear face (e.g., the rear face 110B in FIG. 1) oriented in a second direction D2 opposite the first direction D1, and a side member 211a (e.g., the side bezel structure 106 in FIG. 1) at least partially surrounding a space (e.g., the space denoted by reference numeral "211b") between the front face 110A and the rear face 110B. According to an embodiment of the disclosure, the electronic device 200 may include a display device 202 disposed on the front face 110A or the top face, and the front face 110A of the housing 201 may be substantially formed by the display device 202. In another embodiment of the disclosure, the electronic device 200 may include a cover member 203 disposed on the rear face (e.g., the rear face 110B in FIG. 2) or the bottom face, and the rear face of the housing 201 may be substantially formed by the cover member 203.

According to various embodiments of the disclosure, the display device 202 or the cover member 203 may include a glass plate or a polymer plate including various coating layers. According to an embodiment of the disclosure, in the display device 202, at least a portion of the region made of a glass plate or a polymer plate is a transparent region, which is capable of transmitting a screen to the outside. According to another embodiment of the disclosure, the cover member 203 may be formed of, for example, coated or colored glass, ceramic, a polymer, a metal (e.g., aluminum, stainless steel (STS), or magnesium), or a combination of at least two of above-mentioned materials.

According to various embodiments of the disclosure, the display device 202 or the cover member 203 may be made of a glass or ceramic material, and a partial region of the display device 202 of the cover member 203 may be disposed adjacent to the metallic material portion of the side member 211a. In an embodiment of the disclosure, when a partial region of the cover member 203, made of a glass or ceramic material, is disposed adjacent to the metallic material portion of the side member 211a, a member or layer made of a synthetic resin may be interposed therebetween so as to prevent direct contact between the glass or ceramic material and the metallic material portion. For example, it is possible to prevent the cover member 203 made of the glass or ceramic material from being damaged by an external impact.

Although the housing 201, the display device 202, and the cover member 203 are described as separate components in various embodiments disclosed herein, this is for brevity of description, and the appearance of the electronic device 200 may substantially be formed by coupling the display device 202 and the cover member 203 to the housing 201. For example, it is noted that the "housing" referred to in a specific embodiment may be understood to include the display device 202 and the cover member 203.

According to various embodiments of the disclosure, the side member 211a may substantially form the side wall of the electronic device 200, for example, the housing 201, and may accommodate the support member 204 or the first printed circuit board 205 in the inner space 211b (e.g., the space between the front face 110A and the rear face 110B). Although not illustrated, wearing bands (e.g., the binding members 150 and 160 in FIGS. 1 and 2) may be provided on the outer surface of the side member 211a so as to allow the user to wear the electronic device 200 on his/her body. In some embodiments of the disclosure, the housing 201 may include a plurality of keys 213c (e.g., side key buttons 103 and 104 in FIG. 1) mounted on the side member 211a, and the plurality of keys 213c may be used as input devices when the electronic device 200 is used. The side member 211a may be partially or entirely made of, for example, an electrically conductive material.

According to various embodiments of the disclosure, the housing 201 may include a wheel key 213a (e.g., the wheel key 102 in FIG. 1) disposed on the front face (e.g., the front face 110A). The wheel key 213a has a substantially circular frame shape and is rotatably coupled to the front face of the housing 201 via a lubrication member 213b and is rotatable in the circumferential direction on the front face of the housing 201. The electronic device 200 may detect the rotation of the wheel key 213a so as to change an operation mode or to perform various functions according to the operation mode. For example, the wheel key 213a may be rotated so as to adjust the volume in a multimedia reproduction mode or to generate a signal for executing a zoom function in a camera mode. In some embodiments of the disclosure, the wheel key 213a or the lubrication member 213b may be combined with a serration structure that provides a sense of operation or click, an optical or mechanical encoder that detects the amount of rotation, or the like.

According to various embodiments of the disclosure, the display device 202 may be mounted on the housing 201 to form the front face of the electronic device 200, for example, the front face 110A of the housing 201. By including, for example, a touch panel, the display device 202 may be utilized as an input device even though it is a display device. For example, the display device 202 may output a screen within a region surrounded by the wheel key 213a, and may detect an input operation, such as a user's touch, drag, hovering input, or the like in the screen-output region.

According to various embodiments of the disclosure, the cover member 203 may be coupled to the housing 201 so as to substantially form the rear face of the electronic device 200 (e.g., the rear face 110B of the housing 201), and to close the inner space of the housing 201. When the user wears the electronic device 200, the cover member 203 is capable of maintaining direct contact with the user's body. In an embodiment of the disclosure, at least some of sensor modules (e.g., the sensor module 111 in FIG. 2), such as electrodes or optical elements for detecting the user's biometric information may be disposed on the cover member 203. In the worn state, the electronic device 200 may detect information about the user's health state, such as a heartbeat, using electrodes or optical elements installed on the cover member 203.

According to various embodiments of the disclosure, the support member 204 may be accommodated in the inner space 211b of the housing 201 so as to be utilized as a structure for mounting or fixing the display device 202 and the first printed circuit board 205. In an embodiment of the disclosure, the support member 204 may be connected to the side member 211a or may be integrally formed with the side member 211a. In another embodiment of the disclosure, the support member 204 may be formed of a metallic material or a non-metallic material (e.g., a polymer) so as to improve the stiffness and electrical stability of the electronic device 200. For example, by including an electrically conductive material, the support member 204 may provide electrical stability to the electronic device 200 while providing rigidity to the electronic device 200. For example, by including the electrically conductive material, the support member 204 may provide a ground structure or an electromagnetic shielding structure within the electronic device 200. In some embodiments of the disclosure, the support member 204 may include a space that accommodates a battery (not illustrated).

According to various embodiments of the disclosure, the battery is a device for supplying power to at least one component of the electronic device 200, and may include, for example, a non-rechargeable primary battery, a rechargeable secondary battery, or a fuel cell. At least a portion of the battery may be disposed to be substantially flush with, for example, the first printed circuit board 205. The battery may be provided as a built-in structure inside the electronic device 200, and may be removably disposed on the electronic device 200 in another embodiment.

According to various embodiments of the disclosure, electronic components, such as a processor, a memory, a communication module, various sensor modules, an interface, or a connection terminal, may be mounted on the first printed circuit board 205. The processor may include, for example, one or more of a central processing unit, an application processor, a Graphics Processing Unit (GPU), a sensor processor, or a communications processor. The memory may include, for example, a volatile memory or a nonvolatile memory. The interface may include, for example, a high-definition multimedia interface (HDMI), a universal serial bus (USB) interface, a secure digital (SD) card interface, or an audio interface. The interface may electrically or physically connect the electronic device 200 to an external electronic device, and may include a USB connector, an SD card, a multimedia card (MMC) connector, or an audio connector.

According to various embodiments of the disclosure, the processor, the memory, and the communication module may be equipped in each integrated circuit chip, or two or more selected components may be integrated into one integrated circuit chip and mounted on the first printed circuit board 205. According to an embodiment of the disclosure, the first printed circuit board 205 may be disposed to face the cover member 203, and may be disposed to face the display device 202 with the support member 204 interposed therebetween. For example, the first printed circuit board 205 may be mounted and supported on the other surface of the support member 204, and may be installed in the housing 201 in the state of being spaced apart from the display device 202.

Although not illustrated, the electronic device 200 may further include an antenna provided in the form of a flat plate or a film. For example, at least one of a near field communication (NFC) antenna, a wireless charging antenna, or a magnetic secure transmission (MST) antenna may be fabricated in the form of a thin film (e.g., a flat coil). These antenna devices may be interposed, for example, between the display device 202 and the support member 204 or between the first printed circuit board 205 and the cover member 203. The above-described antenna may perform short-range communication with an external device, may wirelessly transmit and receive power required for charging, and may transmit a magnetic-based signal including a short distance communication signal or payment data.

Figure 5:
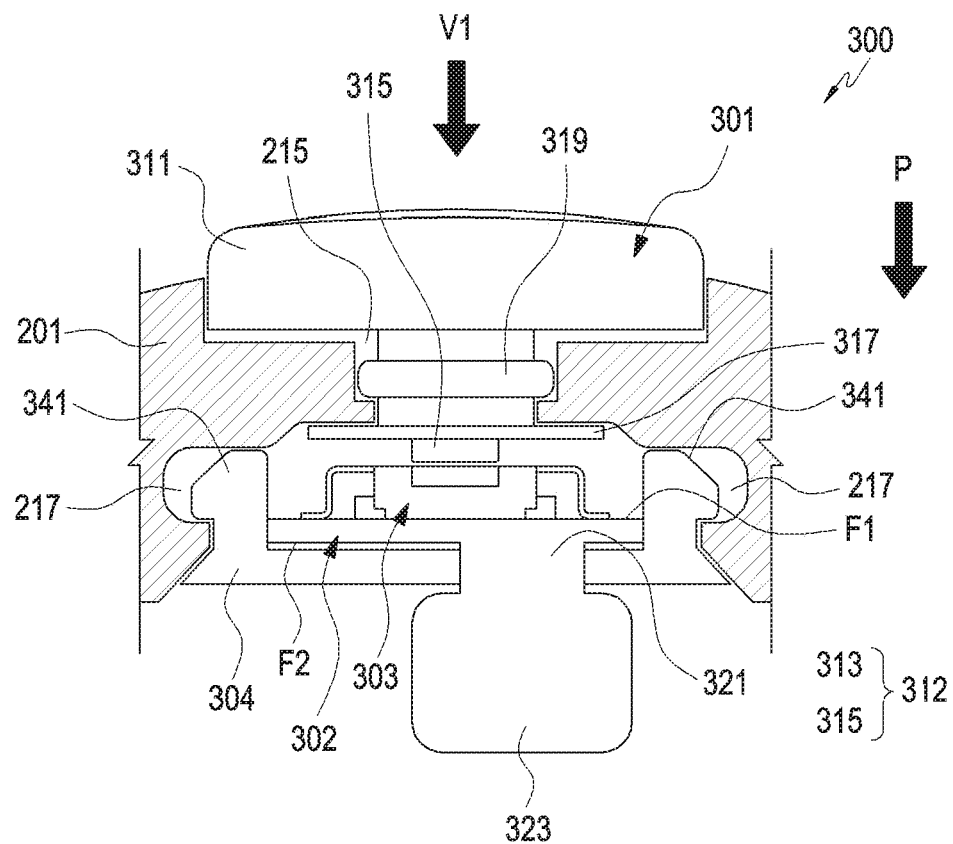
FIG. 5 is a cross-sectional view illustrating an arrangement of a biometric information detection electrode in an electronic device according to an embodiment of the disclosure.

FIG. 5 is a cross-sectional view illustrating an arrangement of a biometric information detection electrode in an electronic device according to an embodiment of the disclosure.

Figure 6:
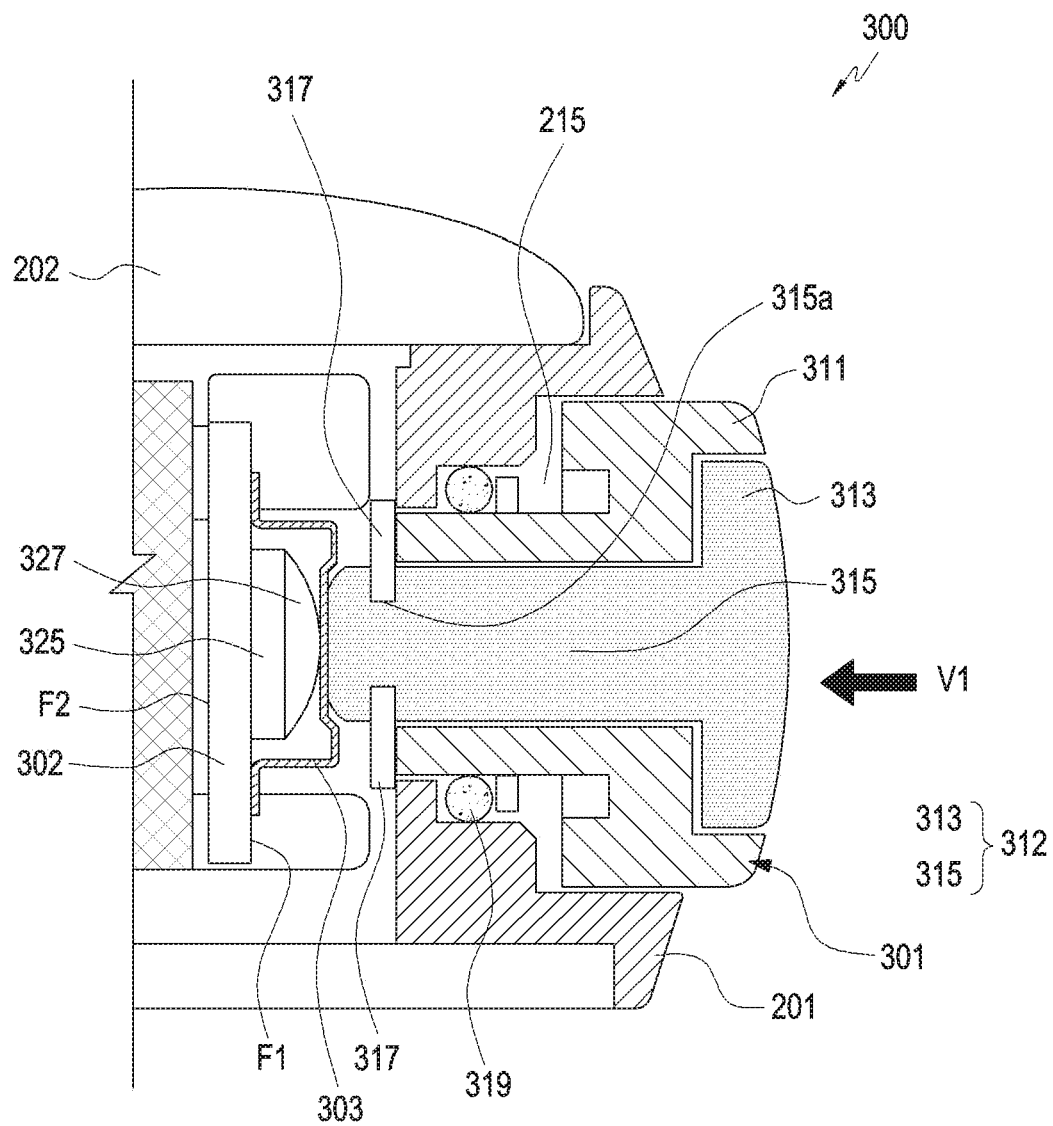
FIG. 6 is a cross-sectional view illustrating an arrangement of a biometric information detection electrode in an electronic device according to an embodiment of the disclosure.

FIG. 6 is a cross-sectional view illustrating an arrangement of a biometric information detection electrode in an electronic device according to an embodiment of the disclosure.

Referring to FIGS. 5 and 6, the electronic device 300 may include an input device including a combination of a second printed circuit board 302, a switch member 325, and/or a button member 301 (e.g., the side key buttons 103 and 104 in FIG. 1 or the plurality of key 213c in FIG. 3). A connection member 303 is provided on the second printed circuit board 302 so as to electrically connect at least a portion (e.g., an electrically conductive member 312) of the button member 301 to the second printed circuit board 302. For example, the button member 301 may include an electrically conductive member 312, and may be electrically connected to the second printed circuit board 302 via the connection member 303. For example, when the electrically conductive member 312 is exposed to the outside of the electronic device 300, it may be used as an electrode or sensor for detecting a biometric signal. Here, the wording "the electrically conductive member is exposed to the outside of the electronic device" may mean that the user is capable of coming into contact with at least a portion of the electrically conductive member 312.

According to various embodiments of the disclosure, the second printed circuit board 302 may be disposed inside the housing 201 of the electronic device 300, and may include a first face F1 and a second face F2 facing away from the first face F1. When the second printed circuit board 302 is disposed inside the housing 201, the first face F1 may be disposed to face the outside of the electronic device 300 in a direction perpendicular to a first direction or a second direction (e.g., the first direction D1 or the second direction D2 in FIG. 3 or FIG. 4). In an embodiment of the disclosure, the second printed circuit board 302 may be formed as a flexible printed circuit board. The second printed circuit board 302 may include an extension portion 321 extending to one side, or a connection portion 323 formed at an end portion of the extension portion 321. For example, the extension portion 321 or the connection portion 323 is for electrically connecting the second printed circuit board 302 with other electronic components (e.g., the first printed circuit board 205 in FIG. 3), and may include a connector structure or various signal wires.

According to various embodiments of the disclosure, the switch member 325 may be disposed on the first face F1, and may include a dome structure 327 disposed to face the outside of the electronic device 300. For example, the switch member 325 may be made of a dome switch. However, this disclosure is not limited thereto, and the switch member 325 may be replaced with another type of structure (e.g., a tact switch) that is operated by the button member 301 so as to generate an electrical signal.

According to various embodiments of the disclosure, the electronic device 300 may further include a fixing member 304. For example, the fixing member 304 is for mounting or fixing the second printed circuit board 302 inside the housing 201, and may be coupled to enclose the second printed circuit board 302 in the state of facing the second face F2. In an embodiment of the disclosure, the electronic device 300 may further include at least one hook 341 disposed on the fixing member 304 and a fixing recess 217 formed in the inner wall of the housing 201. A plurality of hooks 341 and a plurality of fixing recesses 217 may be provided, and the plurality of hooks 341 may be engaged with the fixing recesses 217. By engaging the plurality of hooks 341 in the fixing recesses 217, the fixing member 304 may be bound to the inner wall of the housing 201. In an embodiment of the disclosure, the second printed circuit board 302 may be fixed between the fixing member 304 and the inner wall of the housing 201.

According to various embodiments of the disclosure, the button member 301 may include the electrically conductive member 312. The button member 301 may be mounted on the housing 201 so as to operate the switch member 325. For example, the button 301 may operate the switch member 325 while performing linear motion or linear reciprocal motion on the housing 201 according to the user's operation P. According to an embodiment of the disclosure, the electronic device 200 may include at least one through hole 215 formed in the housing 201. The through hole 215 may be formed in a side member (e.g., the side bezel structures 106 or 211a of FIG. 1 or FIG. 3), and may be aligned with the switch member 325. For example, the button member 301 may be at least partially inserted into the through hole 215, and inside the housing 201, one end of the button member 301 may be located adjacent to the switch member 325. In the state of being inserted into the through hole 215, at least a portion of the button member 301, for example, at least a portion of the electrically conductive member 312 (e.g., a first contact portion 313) may be exposed to the outside of the housing 201.

According to various embodiments of the disclosure, the button member 301 may include a guide portion 311, which at least partially encloses the electrically conductive member 312. The guide portion 311 may insulate the electrically conductive member 312 from other structures (e.g., the housing 201), and may provide a decorative effect on the exterior of the electronic device 300. In the state in which the button member 301 is inserted into the through hole 215, the guide portion 311 may come into contact with the housing 201. For example, at least a portion of the outer peripheral surface of the guide portion 311 may face the inner wall of the through hole 215. In an embodiment of the disclosure, the electrically conductive member 312 may include a first contact portion 313 exposed to the outside of the housing 201 and a second contact portion 315 extending from the first contact portion 313. The second contact portion 315 may be disposed to penetrate the guide portion 311, and at least a portion of the second contact portion 315 may be located inside the housing 201. For example, one end or one end surface of the second contact portion 315 may be arranged to be in contact or to be capable of coming into contact with the switch member 325.

According to various embodiments of the disclosure, the button member 301, for example, the electrically conductive member 312 may include an engaging recess 315a. The engaging recess 315a may be formed in the outer peripheral surface at one end portion of the second contact portion 315. In an embodiment of the disclosure, an engaging member 317, for example, a C-ring or an E-ring, may be fastened to the engaging recess 315a. The engaging member 317 may be supported on the inner wall of the housing 201 in the state of being fastened to the engaging recess 315a. For example, by fastening the engaging member 317 in the state in which the button member 301 is inserted into the through hole 215, the button member 301 may be restrained in the housing 201.

According to various embodiments of the disclosure, when the engaging member 317 is made of an electrically conductive material, and the housing 201 is formed of an electrically conductive material around the through hole 215, an insulating member (not illustrated) may be further disposed between the inner wall of the housing 201 and the engaging member 317. For example, an insulating structure may be provided between the electrically conductive member 312 and the housing 201. When the housing 201 is formed of an insulating material around the engaging member 317 or the through hole 215, the insulating member may not be disposed.

According to various embodiments of the disclosure, a sealing member 319 may be disposed within the through hole 215. The sealing member 319 is, for example, an O-ring made of an elastic material (e.g., rubber or silicone), and is capable of sealing a gap between the outer peripheral surface of the guide portion 311 and the inner wall of the through hole 215. For example, the sealing member 319 is capable of preventing foreign matter from being introduced into the inside of the housing 201 through the through hole 215.

According to various embodiments of the disclosure, the connection member 303 may be disposed on the first face F1 so as to at least partially overlap the switch member 325. For example, when viewed from above the first face F1 (V1), a portion of the connection member 303 may be located to cover at least a portion of the switch member 325. According to an embodiment of the disclosure, the connection member 303 may be mounted in the state of being electrically connected to one of the signal wires provided on the second printed circuit board 302, and may come into contact with the button member 301 (e.g., at least the electrically conductive member 312). For example, the connection member 303 may electrically connect the button member 301 (e.g., the electrically conductive member 312) to the second printed circuit board 302.

According to various embodiments of the disclosure, the electrically conductive member 312 may be used as an electrode for detecting a biometric signal by being electrically connected to the second printed circuit board 302 and insulated from other structures (e.g., the housing 201). For example, when the user's body comes into contact with a portion of the electrically conductive member 312 (e.g., the first contact portion 313) exposed to the outside, the electronic device 300 may detect the user's biometric information using the electrically conductive member 312. The configuration for detecting the user's biometric information using the electrically conductive member 312 will be described below with reference to FIG. 12.

The connection member 303 will be described below with reference to FIG. 7.

Figure 7:
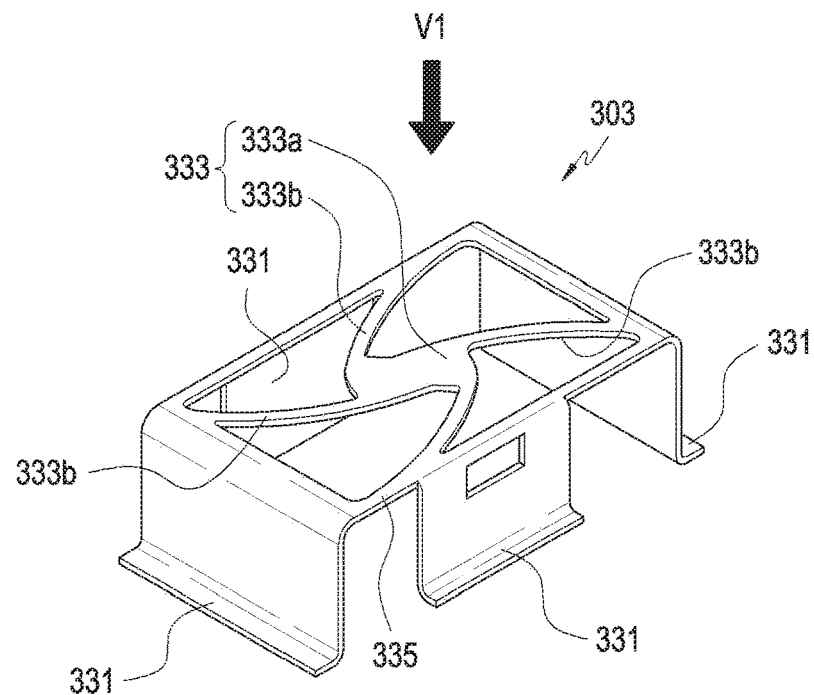
FIG. 7 is a perspective view illustrating a connection member of an electronic device according to an embodiment of the disclosure.

FIG. 7 is a perspective view illustrating a connection member of an electronic according to an embodiment of the disclosure.

Referring to FIG. 7, the connection member 303 may at least partially include a plate-shaped portion, and may include an electrically conductive material. In an embodiment of the disclosure, the connection member 303 may be mounted on or fixed to the second printed circuit board 302. For example, the connection member 303 may be disposed to be in contact with the button member 301 (e.g., the electrically conductive member 312) so as to provide an elastic force. For example, the connection member 303 may provide an elastic force in a direction to cause the button member 301 to protrude to the outside of the housing 201. In an embodiment of the disclosure, when there is not a user's operation (e.g., the user's operation P in FIG. 5), for example, in the state in which there is no pressing operation, the button member 301 may protrude to the outside of the housing 201 by the elastic force of the connection member 303. In another embodiment of the disclosure, since the engaging member 317 fastened to the electrically conductive member 312 is supported on the inner wall of the housing 201, the button member 301 may be maintained in the state of being mounted in the housing 201 while being provided with the elastic force of the connection member 303.

According to various embodiments of the disclosure, the connection member 303 may include at least one fixing portion 331 or a plate-shaped support portion 333 extending from the fixing portion 331. In an embodiment of the disclosure, a plurality of the fixing portions 331 may be formed on respective edges of the support portion 333. According to an embodiment of the disclosure, the fixing portions 331 may be attached to the first face F1 in a protruding state. In an embodiment of the disclosure, one end portion of each fixing portion 331 may be fixed to the second printed circuit board 302. For example, the one end portion of each fixing portion 331 may be electrically connected to a signal wire formed on the second printed circuit board 302.

According to various embodiments of the disclosure, the support portion 333 may be bent from the fixing portions 331 and may be disposed substantially parallel to the first face F1. For example, when viewed from above the first face F1 (V1), at least a portion of the support portion 333 may overlap at least a portion of the switch member 325, and may come into contact with the button member 301 (e.g., the electrically conductive member 312). In an embodiment of the disclosure, the elastic force of the connection member 303 may be substantially provided to the button member 301 through the support portion 333, and the electrically conductive member 312 may be electrically connected to the support portion 333. In some embodiments of the disclosure, when the button member 301 is operated (P), the support portion 333 may come into direct contact with the switch member 325 (e.g., the dome structure 327 in FIG. 6). In an embodiment of the disclosure, when the button member 301 or the electrically conductive member 312 is used as an electrode for biometric signal detection, the support portion 333 and the switch member 325 (e.g., the dome structure 327 in FIG. 6) may be insulated from each other.

According to various embodiments of the disclosure, the support portion 333 may include a contact piece 333a and a plurality of elastic pieces 333b. The contact piece 333a is a portion that comes into contact with the button member 301 or the electrically conductive member 312 so as to provide an elastic force thereto or is electrically connected to the button member 301 or the electrically conductive member 312, and may be located in the center of the support portion 333 when viewed from above the first face F1 (V1). Each of the plurality of elastic pieces 333b may extend from the contact piece 333a, and may connect the contact piece 333a to the fixing portions 331. The plurality of elastic pieces 333b provide an elastic force to cause the button member 301 to protrude to the outside of the housing 201 or to maintain the engaging member 317 in the state of being in close contact with the inner wall of the housing 201.

According to various embodiments of the disclosure, each of the plurality of elastic pieces 333b may at least partially extend along a curved trajectory when viewed from above the first face F1. In an embodiment of the disclosure, the trajectory in which the plurality of elastic pieces 333b extend may have a zigzag shape or a meanderline shape. In another embodiment of the disclosure, the plurality of elastic pieces 333b may be arranged to be symmetrical to each other with respect to the contact piece 333a, regardless of the shapes thereof (e.g., the extension trajectory). In another embodiment of the disclosure, the arrangement of the plurality of elastic pieces 333b may have a vortex shape centered on the contact piece 333a. The arrangement of the plurality of elastic pieces 333b may substantially align the elastic force provided by the support portion 333 in a direction perpendicular to the first face F1. For example, the arrangement of the plurality of elastic pieces 333b may align the direction in which the elastic force of the support portion 333 acts to be parallel to or coincident with the direction in which the button member 301 linearly moves or linearly reciprocates.

According to various embodiments of the disclosure, the connection member 303 may further include a frame structure 335. In an embodiment of the disclosure, the contact piece 333a or the plurality of elastic pieces 333b may be disposed substantially within an area defined by the frame structure 335, and may be disposed in one plane together with the frame structure 335. For example, the contact piece 333a and/or the plurality of elastic pieces 333b may be formed by partially removing the support portion 333, which is a plate-shaped metal sheet or a metal plate. In some embodiments of the disclosure, the frame structure 335 may be formed by a portion of the metal sheet or metal plate forming the support portion 333, and the support portion 333 may substantially form a plate shape with the frame structure 335. The fixing portions 331 may be substantially connected to the plurality of elastic piece 333b via the frame structure 335. The frame structure 335 and the plurality of elastic pieces 333b are described as separate components in describing this embodiment. However, it is noted that these are divided based on actions or functions provided by the respective portions of the support 333 and the disclosure is not limited thereto. For example, in various embodiments disclosed herein, the plurality of elastic pieces 333b may be defined as a configuration including the frame structure 335, and may be understood as a structure in which a plurality of elastic leads extending from the frame structure 335 are connected to the contact piece 333a.

Hereinafter, various modifications of the connection member 303 will be described with reference to FIGS. 8 to 11. In describing various modifications of the connection member 303, the components that can be easily understood through the embodiments of FIGS. 5 to 10 may be denoted by the same reference numerals or the reference numerals may be omitted, and the detailed descriptions thereof may also be omitted.

Figure 8:
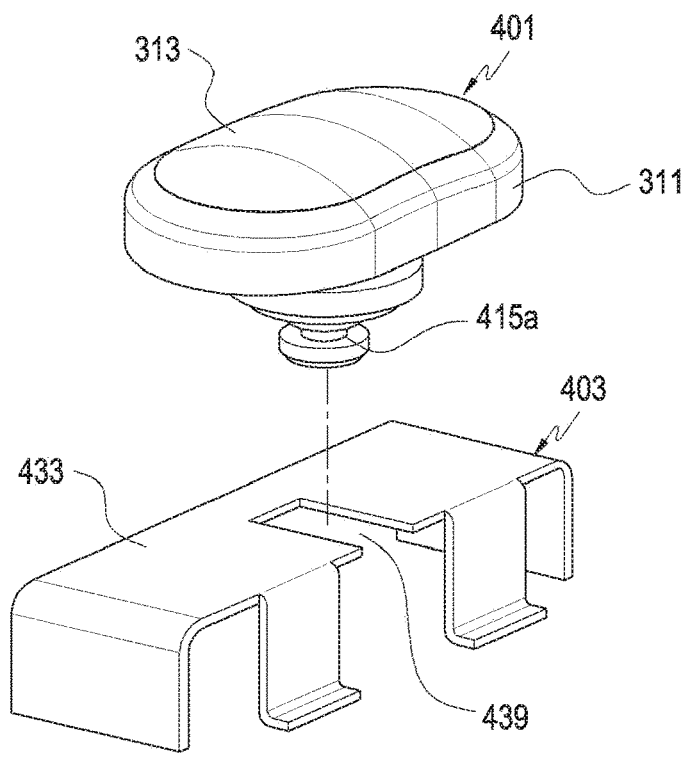
FIG. 8 is an exploded perspective view illustrating a modification of a connection member of an electronic device according to an embodiment of the disclosure.

FIG. 8 is a perspective view illustrating a modification of a connection member of an electronic device according to an embodiment of the disclosure.

Figure 9:
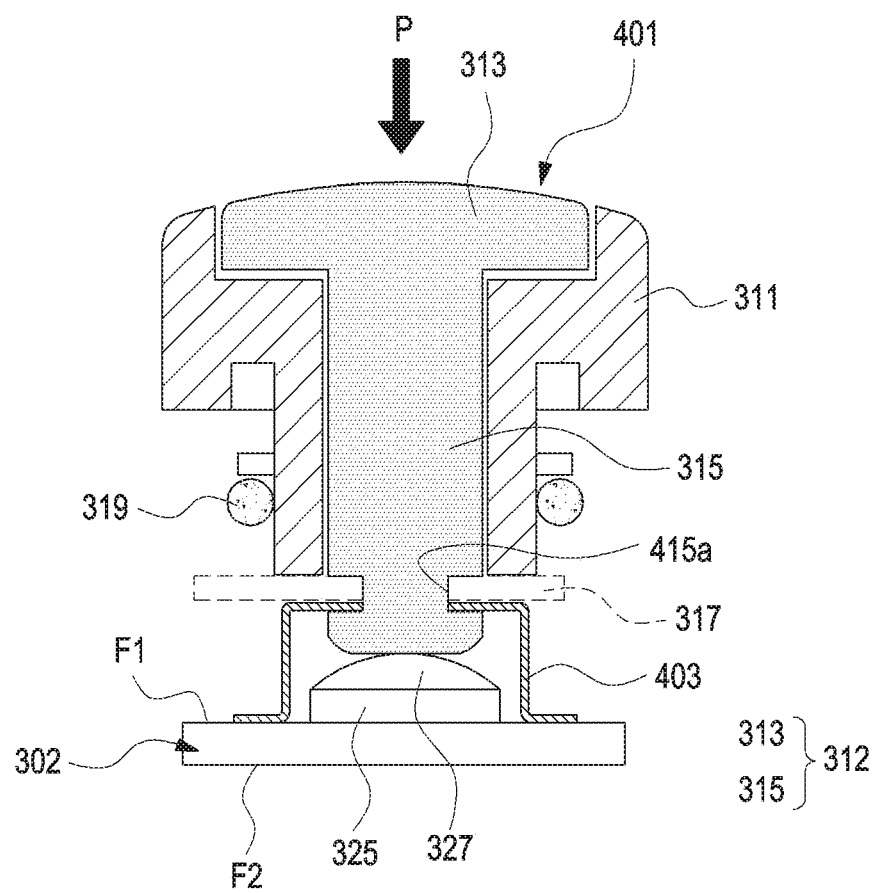
FIG. 9 is a cross-sectional view illustrating a modification of a connection member of an electronic device according to an embodiment of the disclosure.

FIG. 9 is a cross-sectional view illustrating a modification of a connection member of an electronic device according to an embodiment of the disclosure.

Referring to FIGS. 8 and 9, the connection member 403 may be electrically connected to the electrically conductive member 312 while being engaged with the electrically conductive member 312 by being engaged in the engaging recess 415a of the button member 401. In an embodiment of the disclosure, the connection member 403 may include a slot 439 formed in a support portion 433 (e.g., the contact piece 333a in FIG. 7), and a portion of the electrically conductive member 312 (e.g., the second contact portion 315) may be inserted into the slot 439 of the connection member 403. When a portion of the electrically conductive member 312 is inserted into the slot 439, at least a portion of the connection member 403 (e.g., a portion of the support portion 433) may be located in the engaging recess 415a. In another embodiment of the disclosure, when an engaging member 317 (e.g., the engaging member 317 in FIG. 5 or FIG. 6) is fastened to the engaging recess 415a, the support 433 may be fixed in the engaging recess 415a. For example, when the engaging member 317 is fastened, the support portion 433 is able to maintain an electrical contact with the electrically conductive member 312, and the connection member 403 is able to provide an elastic force so as to cause the button member 401 to linearly move or linearly reciprocate.

According to various embodiments of the disclosure, in the structure in which the connection member 403 is engaged with the electrically conductive member 312, one end or one end surface of the electrically conductive member 312 (e.g., the second contact portion 315) may be disposed to be in contact with or come into contact with the switch member 325 (e.g., the dome structure 327). For example, when there is a user's operation P, one end of the electrically conductive member 312 may come into direct contact with the switch member 325 (e.g., the dome structure 327). In an embodiment of the disclosure, when the button member 301 (e.g., the electrically conductive member 312) is used as an electrode or a sensor for biometric signal detection, an insulating member (or an insulating layer) (not illustrated) may be included between one end of the electrically conductive member 312 and the switch member 325 (e.g., the dome structure 327).

Figure 10:
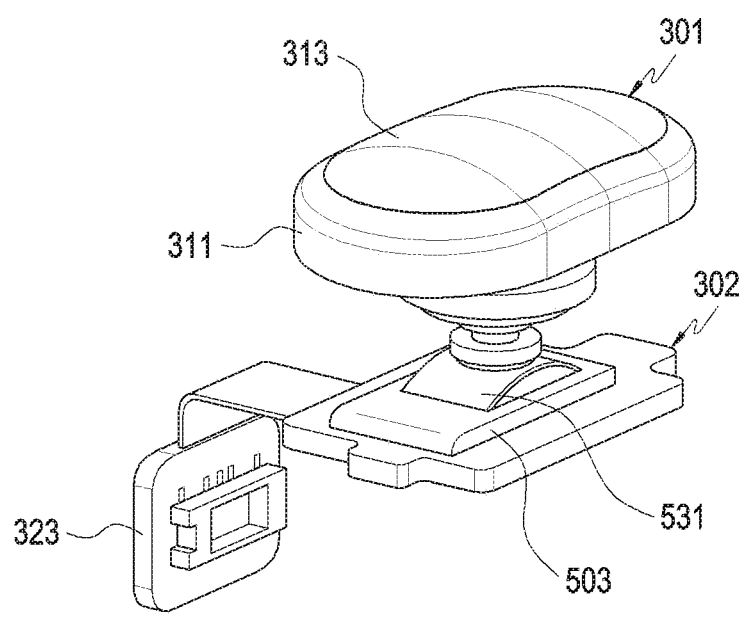
FIG. 10 is a perspective view illustrating a modification of a connection member of an electronic device according to an embodiment of the disclosure.

FIG. 10 is a perspective view illustrating a modification of a connection member of an electronic device according to an embodiment of the disclosure.

Figure 11:
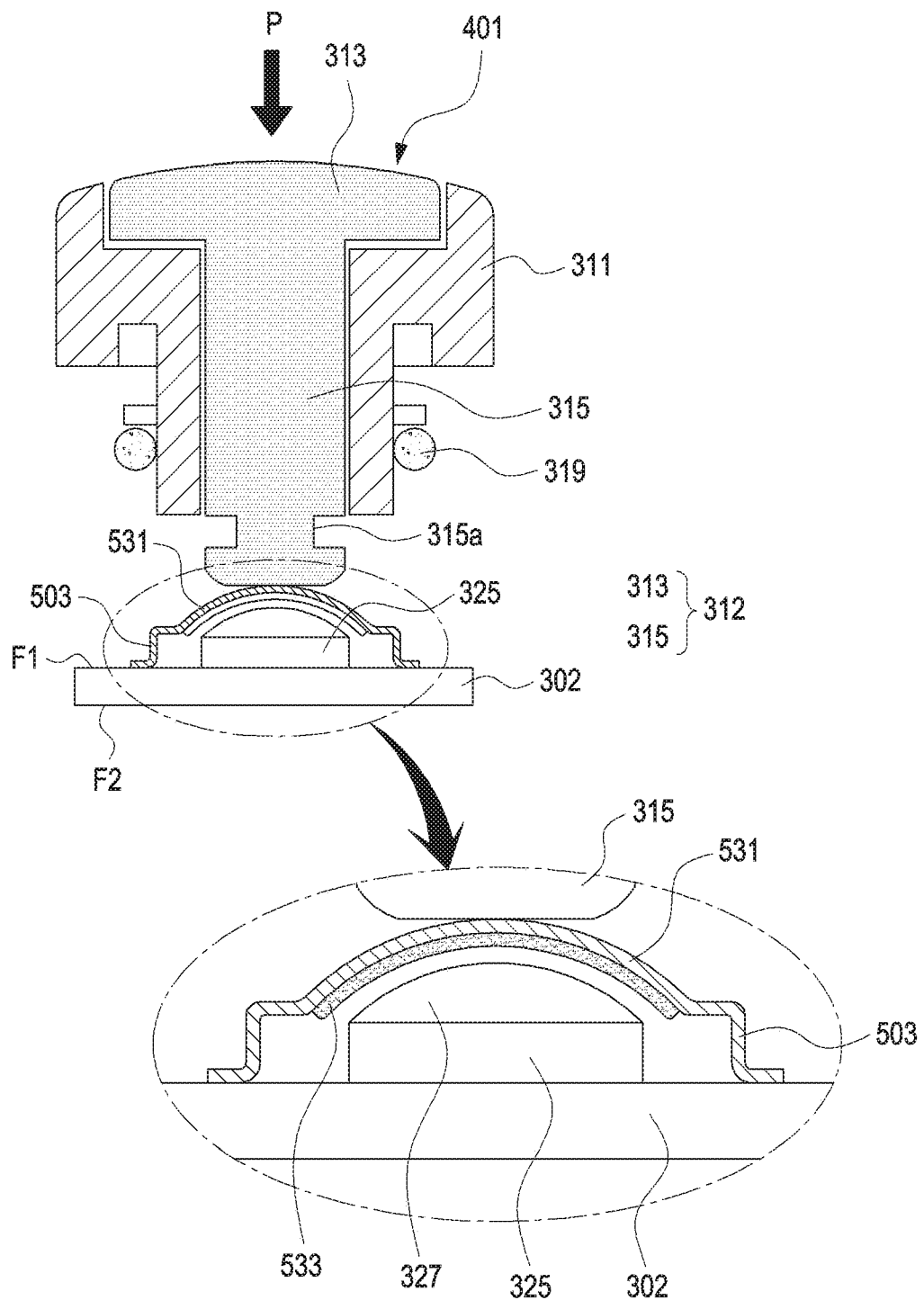
FIG. 11 is a cross-sectional view illustrating a modification of a connection member of an electronic device according to an embodiment of the disclosure.

FIG. 11 is a cross-sectional view illustrating a modification of a connection member of an electronic device according to an embodiment of the disclosure.

Referring to FIGS. 10 and 11, a connection member 503 may include a curved surface portion 531 corresponding to the dome structure 327 of the switch member 325. For example, the curved surface portion 531 may be formed on a support portion (e.g., the support portion 333 in FIG. 7) of the connection member 503 to correspond to the dome structure 327. In some embodiments of the disclosure, the support portion (e.g., the support portion 333 in FIG. 7) of the connection member 503 may have a solid plate shape in which no portion is removed, and the curved surface portion 531 may be formed by deforming a portion of the support portion between cut lines formed to symmetrical to each other. In another embodiment of the disclosure, similar to the embodiment of FIG. 7, the curved surface portion 531 may be formed as a structure including the contact piece 333a and the plurality of elastic pieces 333b of FIG. 7.

According to various embodiments of the disclosure, the curved surface portion 531 may be disposed to correspond to the dome structure 327, and may come into contact with one end or one end surface of the electrically conductive member 312 (e.g., the second contact portion 315). For example, the connection member 503 may provide an elastic force to the button member 301 via the curved surface portion 531, and may electrically connect the electrically conductive member 312 to the second printed circuit board 302. In an embodiment of the disclosure, when there is a user's operation P, at least a portion of the curved surface portion 531 may come into contact with the switch member 325 (e.g., the dome structure 327). In an embodiment of the disclosure, an insulating layer 533 may be included between the curved surface portion 531 and the switch member 325 (e.g., the dome structure 327). For example, the insulating layer 533 may be an insulating coating or insulating tape provided on the inner surface (e.g., the lower side in FIG. 11)

of the curved surface portion 531. In another embodiment of the disclosure, the insulating layer 533 may be provided on the surface of the dome structure 327.

Figure 12:
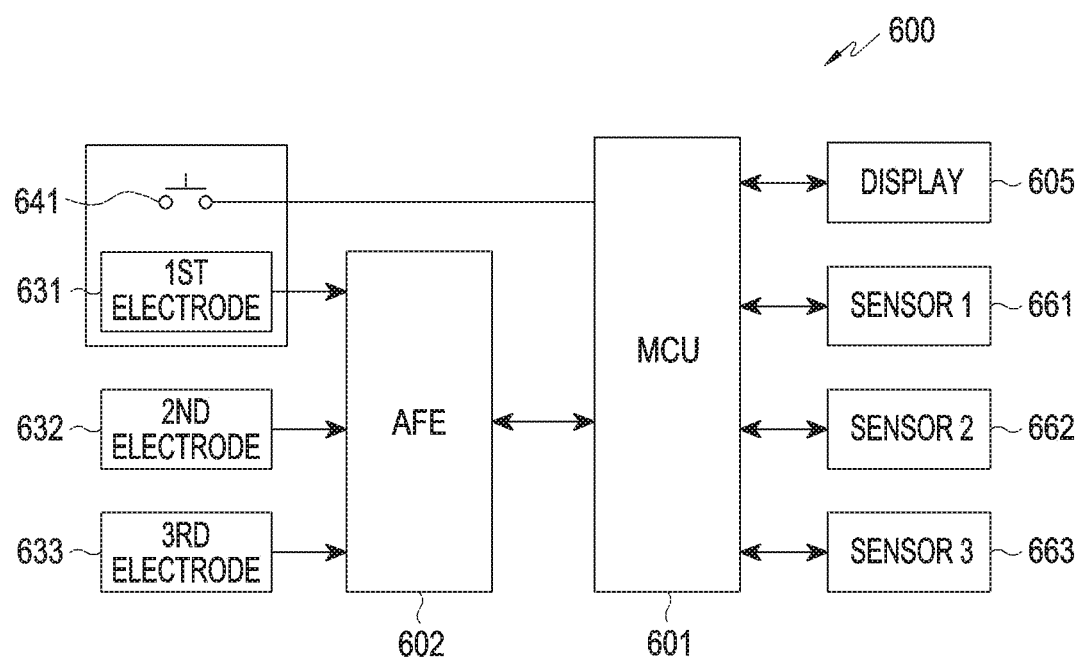
FIG. 12 is a block diagram illustrating an electronic device according to an embodiment of the disclosure.

FIG. 12 is a block diagram illustrating an electronic device according to embodiment of the disclosure.

Referring to FIG. 12, an electronic device 600 may include a processor (e.g., a microcontroller unit (MCU) 601), an analog front end (AFE) 602 (e.g., an analog-to-digital converter (ADC)), a plurality of electrodes 631, 632, and 633, a switch member 641, sensors 661, 662, and 663, and/or a display 605 (e.g., the display device 202 in FIG. 3). As described above with reference to the embodiments of FIGS. 1 to 4, it is noted that the electronic device 600 may include various electronic components, such as a memory, a communication module, a battery, and an antenna connection terminal, which are omitted in FIG. 12.

According to various embodiments of the disclosure, among the plurality of electrodes 631, 632, and 633, a first electrode 631 is, for example, the electrically conductive member 312 of FIGS. 5 to 11, and may be electrically connected to the printed circuit board (e.g., the second printed circuit board 302 in FIG. 5) through a connection member (e.g., the connection member 303, 403, or 503 in FIGS. 5 to 11). For example, the first electrode 631 may be electrically connected to the analog front end 602. Among the plurality of electrodes 631, 632, and 633, a second electrode 632 and/or a third electrode 633 may be any of electrodes (e.g., the sensor module 111 in FIG. 2) disposed in a housing (e.g., the housing 110 in FIG. 1 or FIG. 2). For example, the second electrode 632 and/or the third electrode 633 may be electrically connected to the analog front end 602.

According to various embodiments of the disclosure, in the state in which the user wears the electronic device 600 (e.g., the electronic devices 100, 200, and 300 in FIGS. 1 to 6), the second electrode 632 and the third electrode 633 may be in contact with the user's body. For example, when the user wears the electronic device 600, at least the second electrode 632 and the third electrode 633 may acquire the user's biometric information. In an embodiment of the disclosure, when the user's body portion other than the portion on which the electronic device 600 is worn comes into contact with the first electrode 631, the electronic device 600 may detect the user's biometric information using the first electrode 631, the second electrode 632, and the third electrode 633. For example, when the user wears the electronic device 600 and comes into contact with the first electrode 631, a flow of an electrical signal may be formed between the first electrode 631 and the second electrode 632 or the first electrode 631 and the third electrode 633 through the user's body, and the electronic device 600 may detect the user's biometric information from the flow of the electrical signal. In some embodiments of the disclosure, when the user brings the right hand into contact with the first electrode 631 in the state the user wears the electronic device 600 on the left wrist, a flow of an electrical signal may be formed over a portion close to the heart on the user's body. For example, when the first electrode 631 (e.g., the electrically conductive member 312) comes into contact with a body portion other than the body portion on which the electronic device 600 is worn, accuracy in acquiring biometric information (e.g., an electrocardiogram) may be improved.

According to various embodiments of the disclosure, the analog front end 602 is, for example, an analog-to-digital converter, and may receive an analog signal through the first electrode 631, the second electrode 632, and/or the third electrode 633 and may convert the received signal into a digital signal. The digital signal converted by the analog front end 602 may be transmitted to a processor, for example, the microcontroller unit 601. The microcontroller unit 601 may be disposed inside a housing (e.g., the housing 201 in FIG. 3), for example, on the first printed circuit board 205 in FIG. 3, and may acquire the user's biometric information based on signal received from the analog front end 602. For example, the microcontroller unit 601 may output the acquired biometric information to the display 605, store the same in a memory, or transmit the same to another electronic device or server through a communication module and/or an antenna. When the biometric information based on the received signal satisfies predetermined conditions, the microcontroller unit 601 may provide a warning signal (e.g., a warning screen or sound) to the user or may send the biometric information to a related institution (e.g., a hospital). For example, the predetermined conditions may include a condition in which the user's health is abnormal.

According to various embodiments of the disclosure, the electronic device 600 may not detect biometric information even when the user's body comes into contact with the first electrode 631 (e.g., the electrically conductive member 312 in FIG. 6), but may detect biometric information for a predetermined time when the switch member 641 (e.g., the switch member 325 in FIG. 6) generates an input signal. For example, the switch member 641 is operated when a button member (e.g., the button member 301 or 401 in FIGS. 5 to 11) is operated, that is, in the state in which the user's body practically comes into contact with the electrically conductive member 312. In an embodiment of the disclosure, the user may execute an instruction for detecting biometric information in the electronic device 600 by operating the switch member 641, for example, by pressing the button members 301 and 401, and the electronic device 600 or the microcontroller unit 601 may detect the user's biometric information based on the operation of the switch member 641.

According to various embodiments of the disclosure, even if the switch member 641 does not operate, the electronic device 600 or the microcontroller unit 601 may detect the user's biometric information when the first electrode 631 (e.g., the electrically conductive member 312 in FIG. 5 or FIG. 6) is in contact with the first electrode 631. For example, in the state in which the electronic device 600 is worn, when the user brings a body portion into contact with the first electrode 631, the electronic device 600 or the microcontroller unit 601 may detect that a flow of a signal is formed between the first electrode 631 and the second electrode 632 (or the third electrode 633) through the user's body. In an embodiment of the disclosure, the electronic device 600 or the microcontroller unit 601 may measure a time for which the signal flow lasts, and may determine whether the signal flow is maintained beyond a predetermined time. When the signal flow is maintained beyond a predetermined time, the electronic device 600 or the microcontroller unit 601 may detect the biometric information by determining that the user wants to measure the biometric information.

In an embodiment of the disclosure, the electronic device 600 or the microcontroller unit 601 may measure or store the user's biometric information from a time point exceeding the predetermined time. In another embodiment of the disclosure, the electronic device 600 or the microcontroller unit 601 may temporarily store a detected signal or signal flow during a predetermined time, and may store a signal or signal flow temporarily stored at a time point exceeding the predetermined time as the user's current biometric information. In another embodiment of the disclosure, the electronic device 600 or the microcontroller unit 601 may store signals up to a predetermined time as biometric information, and may further detect or store the user's biometric information for an additional time from the time point exceeding the predetermined time.

According to various embodiments of the disclosure, the sensors 661, 662, and 663 may be, for example, part of the sensor module 111 in FIG. 2, and may be any one of a gesture sensor, a gyro sensor, an atmospheric pressure sensor, a magnetic sensor, an acceleration sensor, a temperature/humidity sensor, a proximity sensor, or an illuminance sensor (not illustrated). The sensors 661, 662, and 663 may generate an electrical signal or data value corresponding to an operating state inside the electronic device 600 or an external operating environment. The microcontroller unit 601 may control other electronic components, such as the display 605, based on information collected through the sensors 661, 662, and 663.

According to various embodiments disclosed herein, an electronic device (e.g., the electronic device 100, 200, 300, or 600 in FIGS. 1 to 6 or FIG. 12) may include: a housing (e.g., the housing 110 or 201 in FIGS. 1 to 6), a printed circuit board (e.g., the second printed circuit board 302 in FIG. 5, FIG. 6, FIG. 9 or FIG. 11) disposed inside the housing and including a first face (e.g., the first face F1 in FIG. 5 or FIG. 6) and a second face (e.g., the second face F2 in FIG. 5 or FIG. 6) that faces away from the first face, a connection member (e.g., the connection member 303, 403, or 503 in FIG. 5, FIG. 6, FIG. 9, or FIG. 11) disposed on the first face and electrically connected to the printed circuit board, a switch member (e.g., the switch member 325 in FIG. 5, FIG. 6, FIG. 9, or FIG. 11) disposed on the first face so as to at least partially overlap the connection member when viewed from above the first face, and a button member (e.g., the button member 301 or 401 in FIG. 5, FIG. 6, FIG. 9, or FIG. 11) including an electrically conductive member (e.g., the electrically conductive member 312 FIG. 5, FIG. 6, FIG. 9, or FIG. 11), and disposed to be capable of operating the switch member. The electrically conductive member may be electrically connected to the connection member.

According to various embodiments of the disclosure, the connection member may at least partially include a plate-shaped portion (e.g., the support portion 333 and/or the frame structure 335 in FIG. 7).

According to various embodiments of the disclosure, the electronic device may further include at least one through hole (e.g., the through hole 215 in FIG. 5 or FIG. 6) formed in the housing, and the button member may be at least partially inserted into the through hole.

According to various embodiments of the disclosure, at least a portion of the electrically conductive member (e.g., the first contact portion 313 in FIG. 5 or FIG. 6) may be exposed to an outside of the housing.

According to various embodiments of the disclosure, the button member may linearly reciprocate within the through hole.

According to various embodiments of the disclosure, the connection member may provide an elastic force in a direction to cause the button member to protrude to the outside of the housing.

According to various embodiments of the disclosure, the connection member may include at least one fixing portion (e.g., the fixing portion 331) disposed on the first face in a protruding state, and having one end fixed to the printed circuit board, and a support portion (e.g., the support portion 333 in FIG. 7) bent from the fixing portion so as to at least partially overlap the switch member when viewed from above the first face. The support portion may be electrically connected to the electrically conductive member by coming into contact with the button member.

According to various embodiments of the disclosure, the support portion may include: a contact piece (e.g., the contact piece 333a in FIG. 7), which is in contact with the button member, and a plurality of elastic pieces (e.g., the plurality of elastic pieces 333b in FIG. 7) extending from the contact piece and connecting the contact piece to the fixing portion.

According to various embodiments of the disclosure, the plurality of elastic pieces may at least partially extend along a curved trajectory when viewed from above the first face.

According to various embodiments of the disclosure, the button member may include: a guide portion (e.g., the guide portion 311 in FIG. 5 or FIG. 6) disposed to be in contact with the housing, a first contact portion (e.g., the first contact portion 313 in FIG. 5 or FIG. 6), as a portion of the electrically conductive member, disposed on the guide portion and exposed to an outside of the housing, and a second contact portion (e.g., the second contact portion 315 in FIG. 5 or FIG. 6), as a portion of the electrically conductive member, extending from the first contact portion and disposed through the guide portion, and wherein the connection member comes into contact with the second contact portion inside the housing.

According to various embodiments of the disclosure, the electronic device may further include at least one through hole formed in the housing and a sealing member (e.g., the sealing member 319 in FIG. 5 or FIG. 6) disposed in the through hole. The outer peripheral surface of the guide portion may be disposed to face the inner wall of the through hole, and the sealing member may seal a gap between the outer peripheral surface of the guide portion and an inner wall of the through hole.

According to various embodiments of the disclosure, the button member may further include an engaging recess (e.g., the engaging recess 315a in FIG. 6) formed around the second contact portion, and the connection member may be engaged with the engaging recess.

According to various embodiments of the disclosure, the electronic device may further include a fixing member (e.g., the fixing member 304 in FIG. 5) coupled to enclose the printed circuit board in a state of facing the second face, a hook (e.g., the plurality of hooks 341 in FIG. 5) formed on the fixing member, and a fixing recess (e.g., the fixing recess 217 in FIG. 5) formed in an inner wall of the housing. The hook is engaged with the fixing recess, and the printed circuit board is fixed between the inner wall of the housing and the fixing member.

According to various embodiments of the disclosure, the electronic device may further include a processor (e.g., the microcontroller unit 601 in FIG. 12) disposed inside the housing and a biometric sensor module (e.g., the sensor module 111 in FIG. 2) at least partially exposed to an outside of the housing. The processor may be configured to detect biometric information through the electrically conductive member and the biometric sensor module when the switch member is operated by the button member.

According to various embodiments of the disclosure, the electronic device may further include a binding member (e.g., the binding members 150 and 160 in FIG. 1 or FIG. 2) connected to at least a portion of the housing and configured to detachably attach the housing to a user's body.

According to various embodiments disclosed herein, an electronic device may include: a housing, a binding member connected to at least a portion of the housing and configured to detachably attach the housing to a user's body, a printed circuit board disposed inside the housing, a connection member disposed on the printed circuit board and electrically connected to the printed circuit board, a button member including an electrically conductive member electrically connected to the connection member, a processor disposed inside the housing, and a biometric sensor module at least partially exposed to an outside of the housing. The processor may be configured to detect a user's biometric information via the electrically conductive member and the biometric sensor module.

According to various embodiments of the disclosure, the connection member may include at least one fixing portion disposed on the first face in a protruding state, and having one end fixed to the printed circuit board, and a support portion bent from the fixing portion. The support portion may include a contact piece, which is in contact with the button member, and a plurality of elastic pieces extending from the contact piece along a curved trajectory and connecting the contact piece to the fixing portion.

According to various embodiments of the disclosure, the electronic device may further include a switch member mounted on the printed circuit board, and the button member may operate the switch member by linearly reciprocating on the housing.

According to various embodiments of the disclosure, the connection member may be disposed so as to at least partially enclose the switch member, and may provide an elastic force in a direction to cause the button member to protrude to the outside of the housing.

According to various embodiments of the disclosure, the switch member may include a dome structure (e.g., the dome structure 327 in FIG. 5 or FIG. 11), and the connection member may be insulated from the switch member and may include a curved surface portion (e.g., the curved surface portion 531 in FIG. 10 or FIG. 11) corresponding to the dome structure.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
   a housing;
   a printed circuit board disposed inside the housing and including a first face and a second face facing away from the first face;
   a switch member disposed on the first face and being electrically connected to the printed circuit board;
   a connection member disposed on the first face and at least partially overlapping the switch member when viewed from above the first face; and
   a button member including an electrically conductive member, the button member being disposed to operate the switch member,
   wherein the button member comprises:
      a guide portion disposed to be in contact with the housing;
      a first contact portion, as a portion of the electrically conductive member, disposed on the guide portion and exposed to an outside of the housing;
      a second contact portion, as a portion of the electrically conductive member, extending from the first contact portion and disposed through the guide portion; and
      an engaging recess formed around the second contact portion, and
   wherein an end of the electrically conductive member is electrically connected to the connection member while the connection member engages the engaging recess.

2. The electronic device of claim 1, wherein the connection member at least partially includes a plate-shaped portion.

3. The electronic device of claim 1, further comprising:
   at least one through hole formed in the housing,
   wherein the button member is at least partially inserted into the at least one through hole.

4. The electronic device of claim 3, wherein at least a portion of the electrically conductive member is exposed to the outside of the housing.

5. The electronic device of claim 3, wherein the button member linearly reciprocates within the at least one through hole.

6. The electronic device of claim 3, wherein the connection member provides an elastic force in a direction to cause the button member to protrude to the outside of the housing.

7. The electronic device of claim 1,
   wherein the connection member comprises:
      at least one fixing portion disposed on the first face in a protruding state, the at least one fixing portion having one end fixed to the printed circuit board; and
      a support portion bent from the at least one fixing portion and at least partially overlapping the switch member when viewed from above the first face, and
   wherein the support portion is electrically connected to the electrically conductive member by coming into contact with the button member.

8. The electronic device of claim 7, wherein the support portion comprises:
   a contact piece contacting the button member; and
   a plurality of elastic pieces extending from the contact piece and connecting the contact piece to the at least one fixing portion.

9. The electronic device of claim 8, wherein the plurality of elastic pieces at least partially extend along a curved trajectory when viewed from above the first face.

10. The electronic device of claim 1, further comprising:
    at least one through hole formed in the housing; and
    a sealing member disposed in the at least one through hole,
    wherein an outer peripheral surface of the guide portion faces an inner wall of the at least one through hole, and
    wherein the sealing member seals a gap between the outer peripheral surface of the guide portion and the inner wall of the at least one through hole.

11. The electronic device of claim 1, further comprising:
    at least one processor disposed inside the housing; and
    a biometric sensor at least partially exposed to the outside of the housing,
    wherein the at least one processor is configured to, based on the switch member being operated by the button member, detect biometric information through the electrically conductive member and the biometric sensor.

12. The electronic device of claim 1, further comprising:
    a binding member connected to at least a portion of the housing and configured to detachably attach the housing to a user's body.

13. An electronic device comprising:
    a housing;
    a binding member connected to at least a portion of the housing and configured to detachably attach the housing to a user's body;

a printed circuit board disposed inside the housing;
a connection member disposed on the printed circuit board and electrically connected to the printed circuit board;
a button member including an electrically conductive member electrically connected to the connection member;
a fixing member coupled to enclose the printed circuit board in a state of facing a second face of the printed circuit board;
a fixing recess formed in an inner wall of the housing;
a hook formed on the fixing member, the hook engaging the fixing recess, wherein the printed circuit board is fixed between the inner wall of the housing and the fixing member;
at least one processor disposed inside the housing; and
a biometric sensor at least partially exposed to an outside of the housing,
wherein the at least one processor is configured to detect a user's biometric information via the electrically conductive member and the biometric sensor.

14. The electronic device of claim 13,
wherein the connection member further comprises:
   at least one fixing portion disposed on a first face of the printed circuit board in a protruding state, the at least one fixing portion having one end fixed to the printed circuit board; and
   a support portion bent from the at least one fixing portion, and
wherein the support portion includes:
   a contact piece contacting the button member; and
   a plurality of elastic pieces extending from the contact piece along a curved trajectory and connecting the contact piece to the at least one fixing portion.

15. The electronic device of claim 13, further comprising:
a switch member mounted on the printed circuit board,
wherein the button member operates the switch member by linearly reciprocating on the housing.

16. The electronic device of claim 15, wherein the connection member at least partially encloses the switch member and provides an elastic force in a direction to cause the button member to protrude to the outside of the housing.

17. The electronic device of claim 14, wherein the plurality of elastic pieces at least partially extend along a curved trajectory when viewed from above the first face.

18. The electronic device of claim 14, further comprising:
at least one through hole formed in the housing,
wherein the button member is at least partially inserted into the at least one through hole.

19. An electronic device comprising:
a housing;
a binding member connected to at least a portion of the housing and configured to detachably attach the housing to a user's body;
a printed circuit board disposed inside the housing;
a switch member mounted on the printed circuit board and including a dome structure;
a connection member disposed on the printed circuit board and electrically connected to the printed circuit board, the connection member being insulated from the switch member and including a curved surface portion corresponding to the dome structure;
a button member including an electrically conductive member electrically connected to the connection member and configured to operate the switch member by linearly reciprocating on the housing;
at least one processor disposed inside the housing; and
a biometric sensor at least partially exposed to an outside of the housing,
wherein the at least one processor is configured to detect a user's biometric information via the electrically conductive member and the biometric sensor.

20. An electronic device comprising:
a housing;
a printed circuit board disposed inside the housing and including a first face and a second face facing away from the first face;
a switch member disposed on the first face and being electrically connected to the printed circuit board;
a connection member disposed on the first face and at least partially overlapping the switch member when viewed from above the first face;
a button member including an electrically conductive member, the button member being disposed to operate the switch member, an end of the electrically conductive member being electrically connected to the connection member;
a fixing member coupled to enclose the printed circuit board in a state of facing the second face;
a hook formed on the fixing member; and
a fixing recess formed in an inner wall of the housing,
wherein the hook engages the fixing recess, and
wherein the printed circuit board is fixed between the inner wall of the housing and the fixing member.

* * * * *